United States Patent [19]
Takachi

[11] Patent Number: 5,921,437
[45] Date of Patent: Jul. 13, 1999

[54] DISPENSER APPARATUS

[76] Inventor: Ken Takachi, 6-59, Koyoen Hinode-cho, Nishinomiya, Hyogo, Japan

[21] Appl. No.: 09/097,687

[22] Filed: Jun. 16, 1998

[30] Foreign Application Priority Data

Jun. 23, 1997 [JP] Japan ................................. 9-166230

[51] Int. Cl.$^6$ .................................................. B67D 5/08
[52] U.S. Cl. ............................................................ 222/63
[58] Field of Search ............................. 222/52, 63, 333; 425/145; 264/40.1

[56] References Cited

U.S. PATENT DOCUMENTS

| | | | |
|---|---|---|---|
| 3,666,141 | 5/1972 | Ma et al. | 222/63 X |
| 3,888,388 | 6/1975 | Mahoney | 222/63 X |
| 4,475,666 | 10/1984 | Bilbrey et al. | 222/63 X |
| 5,348,585 | 9/1994 | Weston | 222/63 X |
| 5,630,527 | 5/1997 | Beebe et al. | 222/63 X |
| 5,662,272 | 9/1997 | Buquet et al. | 222/63 X |
| 5,711,483 | 1/1998 | Hays | 222/63 |

*Primary Examiner*—Kevin P. Shaver
*Attorney, Agent, or Firm*—McDermott, Will & Emery

[57] ABSTRACT

In a dispenser apparatus, after a piston is moved toward the front end side by a first piston control unit by a distance corresponding to a prescribed injection amount (Q) and an arbitrarily decided additional amount (+α)(to position B2), the piston is moved toward the rear end side by a distance corresponding to an arbitrarily decided additional amount (−α)(to position B3) in order to decrease the pressure applied to an aerobic sealing agent. Accordingly, a dispenser apparatus which can introduce an accurate amount of highly viscous liquid within a prescribed time can be provided.

2 Claims, 5 Drawing Sheets

DISPENSER APPARATUS

BACKGROUND OF THE INVENTION

1. Field of the Invention

The present invention relates to a dispenser apparatus, and more particularly relates to a structure of a dispenser apparatus which can introduce an accurate amount of highly viscous liquid into a prescribed portion within a prescribed time.

2. Description of the Background Art

Conventionally, when one member is fixed to the other member having a threaded hole formed therein using a screw, an anaerobic sealing agent is occasionally used for locking the screw in the threaded hole in advance. The technique is hereinafter described referring to FIGS. 5 and 6. FIG. 5 is a plan view of the member, and FIG. 6 is a cross section of the member in FIG. 5 viewed in the direction of the arrow.

Referring to FIG. 5, when threaded holes 52 are formed in the four corners of a member 50, for example, a prescribed amount of an anaerobic sealing agent 1 is automatically injected into threaded hole 52 using a dispenser apparatus. Referring to FIG. 6, when a screw 53 is tightened in threaded hole 52 in which anaerobic sealing agent 1 is injected, anaerobic sealing agent 1 fills a gap between screw 53 and threaded hole 52 and seals them. Anaerobic sealing agent 1 thereafter sets, and screw 53 is fixedly attached to threaded hole 52 so that a member 54 is fastened to member 50 by screw 53.

When a prescribed amount of anaerobic sealing agent 1 having high viscosity is injected, a dispenser apparatus 100 shown in FIG. 7 is utilized. A structure of dispenser apparatus 100 is briefly described below.

A cylinder 10 constituted by a cylindrical body having an inject portion 10a for anaerobic sealing agent 1 at its front end side and an opening 10c at its rear end side is attached to dispenser unit 100. A piston 10b is provided movably between the front and rear end sides of cylinder 10 for defining a space inside cylinder 10 in which anaerobic sealing agent 1 is enclosed.

In the condition shown in FIG. 7, the inside of cylinder 10 is filled with anaerobic sealing agent 1. A plunger 104 is connected to piston 10b for driving piston 10b provided to dispenser apparatus 100.

Considering the effective use of the anaerobic sealing agent and the efficient operation, the most important thing for cylinder 10 having the structure above in the introduction of anaerobic sealing agent 1 is that a prescribed amount of anaerobic sealing agent 1 is accurately injected within a prescribed time. If the injected amount of anaerobic sealing agent 1 is small, for example, the agent would not function as a locking agent for a screw. On the other hand, if the injected amount of anaerobic sealing agent 1 is large, anaerobic sealing agent 1 overflows from the threaded hole, and removal of the overflow of anaerobic sealing agent 1 is required.

When anaerobic sealing agent 1 is pushed to the front end side following the movement of piston 10b, a high pressure is applied to anaerobic sealing agent 1 within cylinder 10 since the inner diameter of cylinder 10 and that of inject portion 10a are widely different from each other. The higher the viscosity of the agent, the higher the pressure applied to anaerobic sealing agent 1. Accordingly, cylinder 10 is caused to expand greatly. Although the expansion of the cylinder 10 can be avoided by forming cylinder 10 from a member having a high rigidity, cylinder 10 is generally produced from a disposable member which is mass-produced in the market. Considering the cost of cylinder 10, a member which inevitably causes any expansion is utilized for cylinder 10.

As a result, when piston 10b is moved by a prescribed distance for introducing a prescribed amount of anaerobic sealing agent 1 into threaded hole 52, an amount of anaerobic sealing agent 1 exceeding a prescribed amount thereof continue to flow from the front end of inject portion 10a still after a prescribed time elapses due to the pressure applied from cylinder 10 to anaerobic sealing agent 1 after cylinder 10 expands. Accordingly, a problem of increase in the amount of the anaerobic sealing agent to be used and decrease in the operating efficiency occurs.

SUMMARY OF THE INVENTION

One object of the present invention is to provide a dispenser apparatus which can introduce an accurate amount of a highly viscous liquid into a prescribed portion within a prescribed time.

A dispenser apparatus according to the present invention has a cylinder attached thereto. The cylinder has a cylindrical body provided with an inject portion at its front end side and an opening at its rear end side, and has a piston attached movably between the front and rear end sides of the body for defining a space inside the body in which a highly viscous liquid is enclosed. The dispenser apparatus includes a piston drive unit for moving the piston toward the front or rear end side, a first piston control unit which outputs to the piston drive unit a signal for moving the piston toward the front end side by a prescribed distance in order to introduce the highly viscous liquid enclosed in the inside of the cylinder into a prescribed portion. The dispenser apparatus further includes a second piston control unit which outputs to the piston drive unit a signal for moving the piston toward the rear end side by a prescribed distance in order to decrease the pressure of the liquid applied to the cylinder after the piston is moved by the first piston control unit by the prescribed distance.

The first piston control unit controls such that the piston is moved toward the front end side by a distance corresponding to a prescribed amount of the highly viscous liquid and an arbitrarily decided amount of additional liquid. The second piston control unit controls such that the piston is moved toward the rear end side by a distance corresponding to the arbitrarily decided amount of additional highly viscous liquid. As a result, the pressure applied to the highly viscous liquid within the cylinder decreases, so that only a prescribed amount of highly viscous liquid can be caused to flow from the front end of the cylinder. An accurate amount of highly viscous liquid can be introduced into a prescribed portion within a prescribed time.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
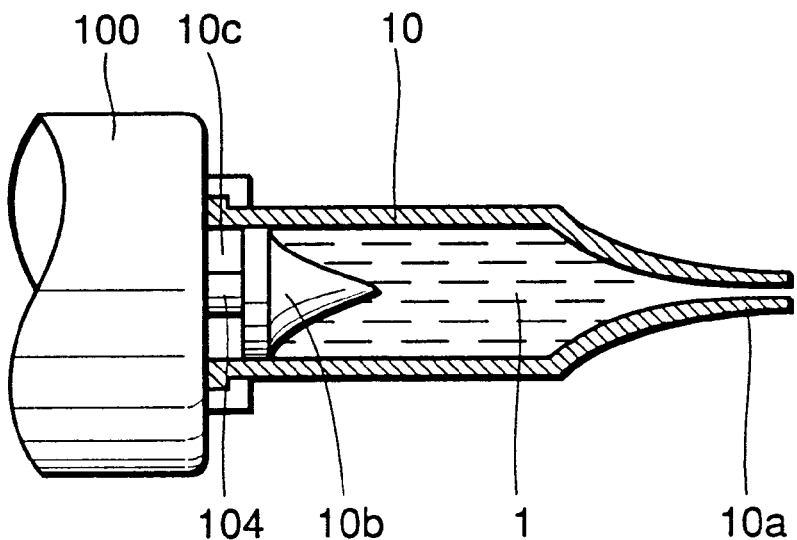
FIGS. 1 and 2 show the first and the second processes for introducing an anaerobic sealing agent into a prescribed portion using a dispenser apparatus for the anaerobic sealing agent according to the embodiment of the invention.

An embodiment of a dispenser apparatus according to the present invention is described referring to the attached figures below. The same reference characters denote the identical or the corresponding parts in the drawings.

Figure 2:
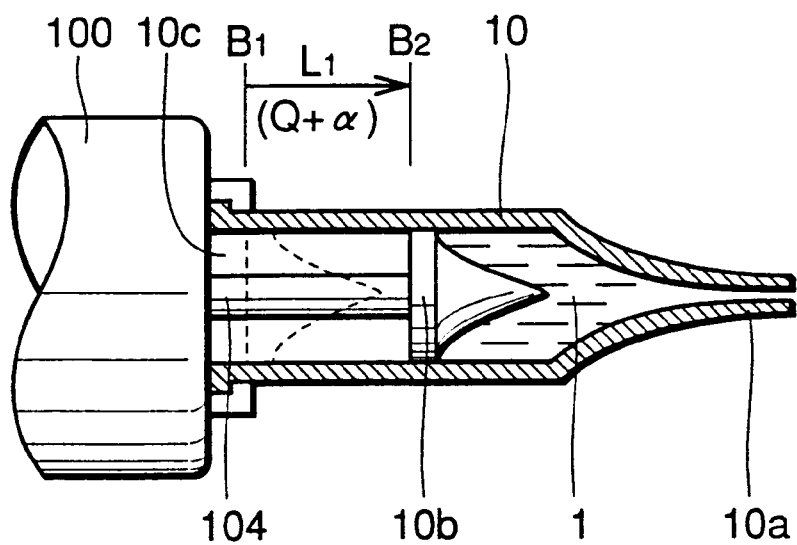
Figure 3:
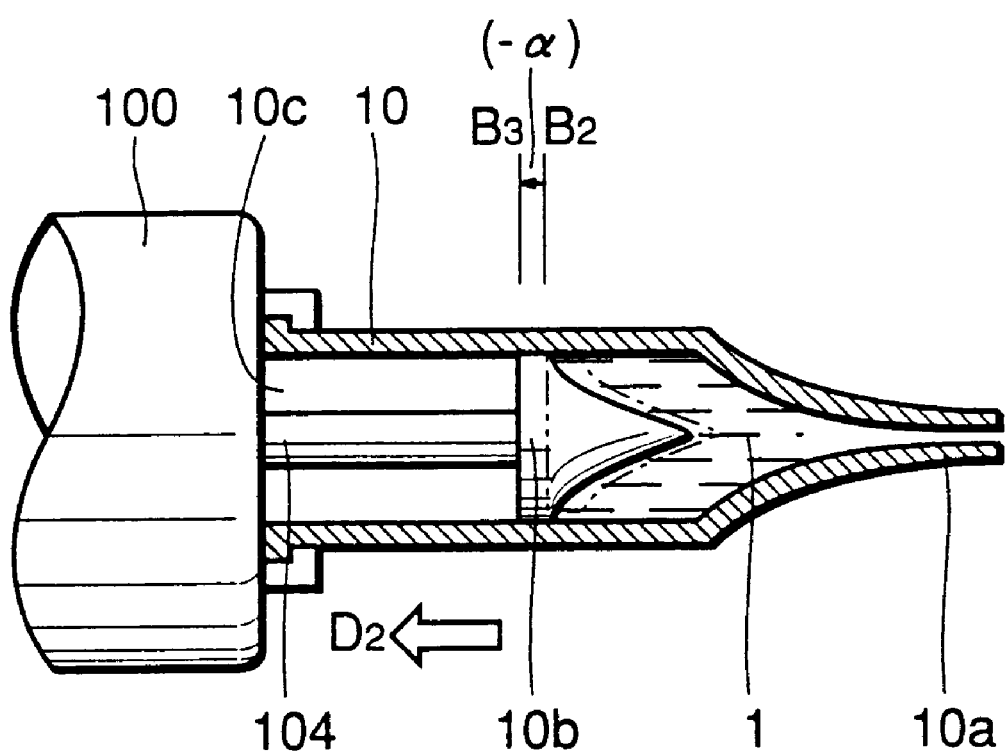
FIG. 3 shows the third process for introducing the anaerobic sealing agent into a prescribed portion using the dispenser apparatus for the anaerobic sealing agent according to the embodiment.

Referring to FIGS. 1–3, a dispenser apparatus for injecting anaerobic sealing agent which is a highly viscous liquid according to the embodiment is described.

Figure 6:
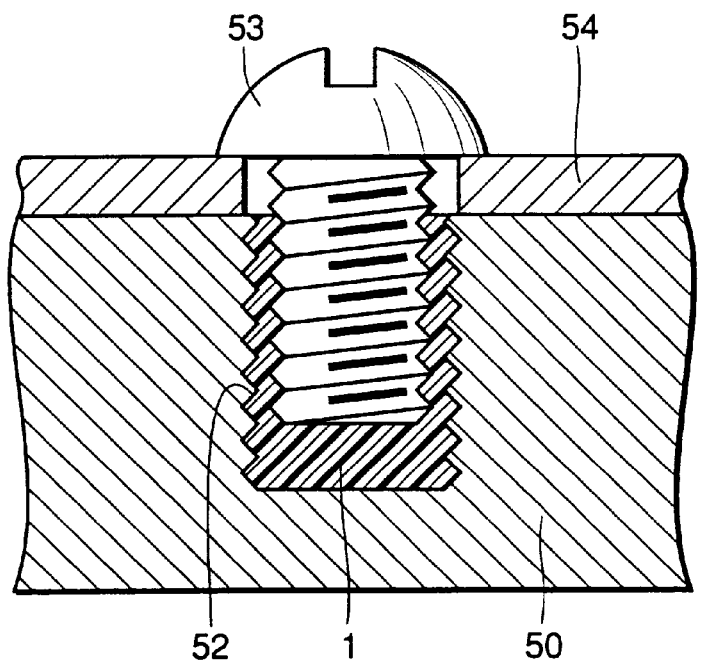
FIG. 6 is a cross section of the member in FIG. 5 viewed in the direction of the arrow X.
Figure 7:
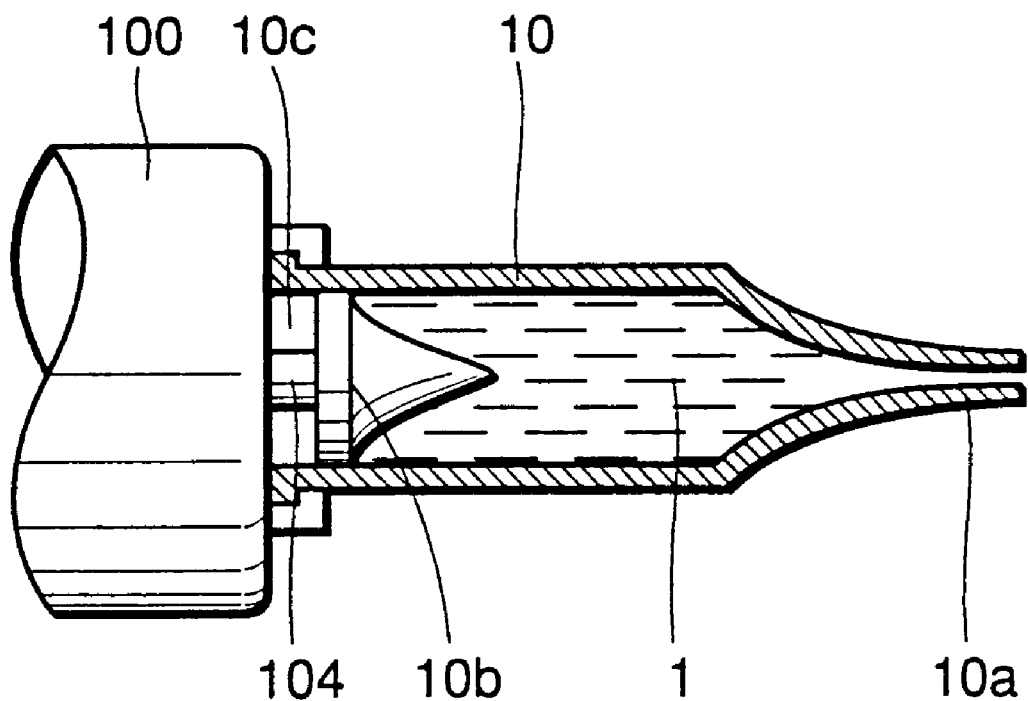
FIG. 7 is a cross section of the structure of a cylinder attached to a dispenser apparatus for an anaerobic sealing agent.

With reference to FIG. 1 first, a cylinder 10 having the same shape as that of one described referring to FIG. 6 is attached to a dispenser apparatus 100. Referring to FIG. 2, in order to introduce a prescribed amount (Q) of anaerobic sealing agent into a prescribed portion, a piston 10$b$ is advanced by a distance L1 by moving a plunger 104 provided to dispenser apparatus 100 by a distance corresponding to the prescribed amount (Q) and an arbitrarily decided additional amount (+α). Assume that the position of piston 10$b$ in the state shown in FIG. 1 is B1, and the position of piston 10$b$ after moved as shown in FIG. 2 is B2.

As shown in FIG. 3, in order to decrease the pressure applied from cylinder 10 to anaerobic sealing agent 1 enclosed in cylinder 10, piston 10$b$ is withdrawn in the direction shown by the arrow D2 by an arbitrarily decided additional amount (−α). Assume that the position of piston 10$b$ at this time is B3. By withdrawing piston 10$b$ by a prescribed amount, the pressure applied from cylinder 10 to the remaining anaerobic sealing agent 1 in cylinder 10 decreases, so that only the prescribed amount (Q) of anaerobic sealing agent 1 can be injected from the front end of inject portion 10$a$.

The amount of the movement of piston 10$b$ is determined considering various parameters that influence the pressure applied to anaerobic sealing agent 1, such as the position of the piston after completion of the introduction of the agent, the inner diameter of cylinder 10, and the speed of the movement of piston 10$b$.

Figure 4:
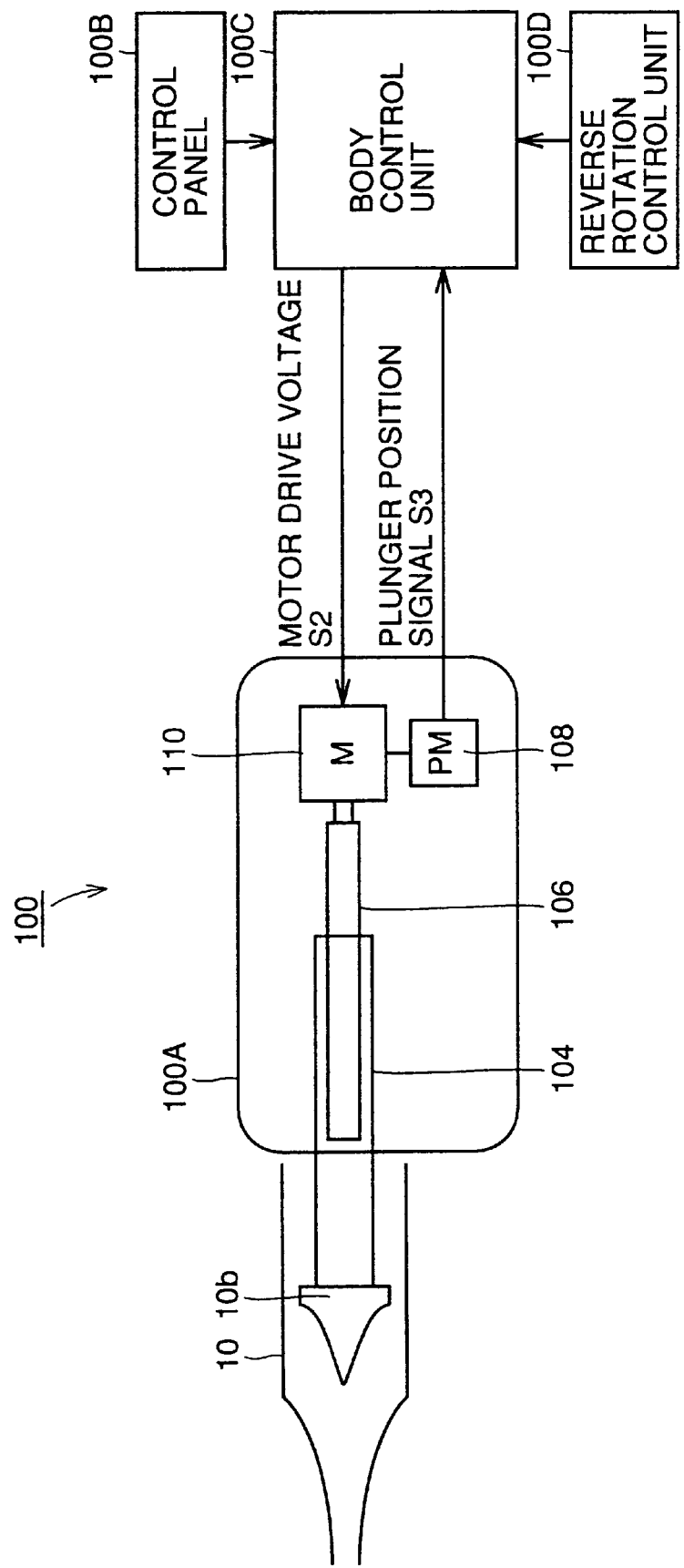
FIG. 4 is a block diagram showing a structure of a dispenser apparatus for an anaerobic sealing agent according to the embodiment.
Figure 5:
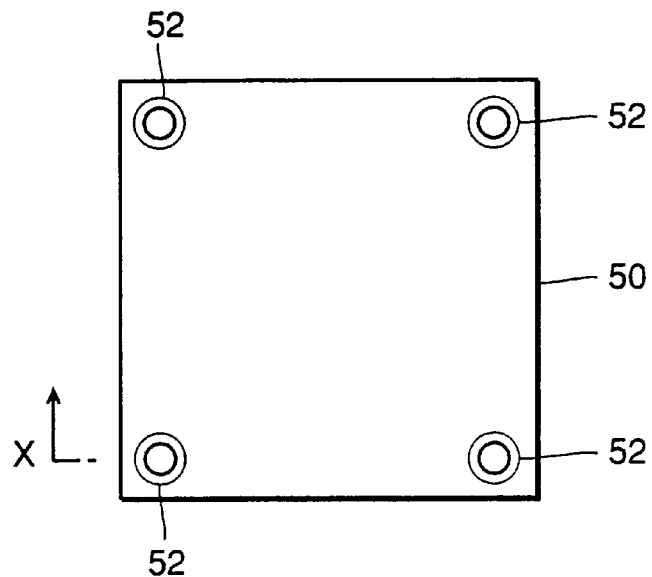
FIG. 5 is a plan view of a member.

With the reference to FIG. 4, a method of controlling dispenser apparatus 100 for realizing the operation shown in FIGS. 1–3 is described.

Dispenser apparatus 100 is provided with a plunger 104 connected to piston 10$b$ located in cylinder 10. Plunger 104 can be moved forward and backward by a ball screw 106 to which the rotation of a motor 110 is transmitted.

A potentiometer 108 for detecting the position of plunger 104 is connected to motor 110, and a plunger position signal S3 provided from potentiometer 108 is supplied to a body control unit 110C.

A motor drive voltage S2 is output from body control unit 100C to motor 110. When an amount of injection of the anaerobic sealing agent into a prescribed portion is inputted to a control panel 100B, a corresponding signal is output from control panel 100B to body control unit 100C, and motor drive voltage S2 is supplied from body control unit 100C to motor 110.

From potentiometer 108, plunger position signal S3 is supplied to body control unit 100C as a feedback signal. An accurate position control of plunger 104 is thus possible, and a prescribed amount of the anaerobic sealing agent can be introduced into a prescribed portion.

Further, a reverse rotation control unit 100D is connected to body control unit 100C. Reverse rotation control unit 100D outputs a signal for reversing the rotation of motor 110 and withdrawing piston 10$b$ by plunger 104 by arbitrarily decided additional amount (−α) after a prescribed amount of the anaerobic sealing agent is introduced.

The amount of movement of piston 10$b$ is determined considering a parameter which influences the pressure applied to the anaerobic sealing agent. If the pressure applied to the anaerobic sealing agent is higher, for example, cylinder 10 expands more, so that the arbitrarily decided additional amount (+α) should be increased considering the expansion. On the other hand, if the pressure applied to the anaerobic sealing agent is lower, cylinder 10 expands less, so that the arbitrarily decided additional amount (+α) is decreased considering the expansion.

Another parameter is a remaining amount of the anaerobic sealing agent after injection of the agent. If the remaining amount of the anaerobic sealing agent after injection is larger, the cylinder 10 expands more, so that the arbitrarily decided additional amount (+α) should be increased considering the expansion. On the other hand, if the remaining amount of the agent after the injection is smaller, cylinder 10 expands less, so that the arbitrarily decided additional amount (+α) is decreased.

Still another parameter is the speed of the movement of piston 10$b$. If the speed of movement of piston 10$b$ is increased in order to enhance the operating efficiency of the injection of the anaerobic sealing agent, the pressure applied to the agent is increased to further expand cylinder 10. Accordingly, the arbitrarily decided additional amount (+α) should be increased considering the expansion. On the other hand, if the speed of the movement of piston 10$b$ is lower, the pressure applied to the anaerobic sealing agent is decreased. Accordingly, cylinder 10 expands less, so that arbitrarily decided additional amount (+α) may be smaller Considering the expansion.

The arbitrarily decided additional amount is also determined by considering various parameters such as the inner diameter of cylinder 10 which influences the pressure applied to the anaerobic sealing agent.

Using the dispenser apparatus according to this embodiment, the pressure applied to the anaerobic sealing agent within the cylinder is decreased by introducing a prescribed amount and an arbitrarily decided additional amount of the anaerobic sealing agent and thereafter moving the piston backward by a prescribed distance corresponding to the arbitrarily decided additional amount, so that only the prescribed amount of the anaerobic sealing agent can be supplied from the front end of the cylinder. As a result, an accurate amount of an aerobic sealing agent can be introduced into a prescribed portion within a prescribed time.

Although description of a dispenser apparatus for introducing an aerobic sealing agent as a highly viscous liquid is given in the embodiment above, the embodiment can be applied to all the dispenser apparatuses for introducing an adhesive, a contrast medium and any other highly viscous liquid other than the anaerobic sealing agent. For example, if the invention is applied to an injector head for medical use for supplying a contrast medium to a patient used for the X-ray diagnosis on circulatory organ, injection of unnecessary amount of contrast medium can be avoided to achieve a proper diagnosis in the optimum state.

Although the present invention has been described and illustrated in detail, it is clearly understood that the same is by way of illustration and example only and is not to be taken by way of limitation, the Spirit and scope of the present invention being limited only by the terms of the appended claims.

What is claimed is:

1. A dispenser apparatus to which a cylinder is attached, the cylinder having a cylindrical body provided with an inject portion at its front end side and an opening at its rear end side and having a piston attached movably between the front and rear end sides of said body for defining a space inside said body in which a highly viscous liquid is enclosed, comprising:

piston drive means for moving said piston toward the front or rear end side;

first piston control means for outputting to said piston drive means a signal for moving said piston toward the front end side by a prescribed distance in order to introduce said highly viscous liquid enclosed in said cylinder into a prescribed portion; and second piston control means for outputting to said piton drive means a signal for moving said piston toward the rear end side by a prescribed distance in order to decrease a pressure of said liquid applied to said cylinder after moving said piston by the prescribed distance by said first piston control means.

2. The dispenser apparatus according to claim 1, wherein said first piston control means controls such that said piston is moved toward the front end side by a distance corresponding to a prescribed amount and an arbitrarily decided additional amount of said highly viscous liquid, and said second piston control means controls such that said piston is moved toward the rear end side by a distance corresponding to said arbitrarily decided additional amount of said highly viscous liquid.

* * * * *